United States Patent [19]

Hartman et al.

[11] Patent Number: 5,164,603

[45] Date of Patent: Nov. 17, 1992

[54] MODULAR SURFACE INSPECTION METHOD AND APPARATUS USING OPTICAL FIBERS

[75] Inventors: Nile F. Hartman, Stone Mountain; James W. Larsen, Douglasville; Carl M. Verber, Atlanta, all of Ga.

[73] Assignee: Reynolds Metals Company, Richmond, Va.

[21] Appl. No.: 731,038

[22] Filed: Jul. 16, 1991

[51] Int. Cl.⁵ .................................. G01N 21/88
[52] U.S. Cl. .......................... 250/572; 250/227.29; 356/237
[58] Field of Search .......... 250/572, 571, 562, 214 A, 250/205, 227.29; 356/430, 237, 446, 447, 448

[56] References Cited

U.S. PATENT DOCUMENTS

| | | | |
|---|---|---|---|
| 3,655,980 | 4/1972 | Bossen | 250/83.3 D |
| 3,859,538 | 1/1975 | Mannonen | 250/572 |
| 3,942,021 | 3/1976 | Barr et al. | 250/572 |
| 3,968,366 | 7/1976 | Asfour | 250/239 |
| 3,975,644 | 8/1976 | Scharf | 250/563 |
| 4,511,803 | 4/1985 | Röss et al. | 250/563 |
| 4,512,662 | 4/1985 | Tobias | 356/380 |
| 4,525,630 | 6/1985 | Chapman | 250/572 |
| 4,559,451 | 12/1985 | Curl | 250/560 |
| 4,634,857 | 1/1987 | Fey | 250/227 |
| 4,639,608 | 1/1987 | Kuroda | 250/578 |
| 4,682,040 | 7/1987 | Hohki et al. | 250/572 |
| 4,709,157 | 11/1987 | Shimizu et al. | 250/572 |
| 4,728,800 | 3/1988 | Surka | 250/572 |
| 4,850,712 | 7/1989 | Abshire | 250/205 |
| 4,914,309 | 4/1990 | Masaharu et al. | 250/572 |

*Primary Examiner*—David C. Nelms
*Assistant Examiner*—K. Shami
*Attorney, Agent, or Firm*—Alan T. McDonald

[57] ABSTRACT

An apparatus 10 for inspecting the surface of an object S moving in the direction of travel 23 relative to the apparatus comprises a modular sensing head assembly 11 including a plurality of sensing head modules 12, 13, each of which includes a number of sensing stations 16–21. Each sensing station includes a light source 77, 81, 84 for generating a line of light extending across substantially the width of the surface of the object and a plurality of optical detector means for detecting light scattered from the line of light by the surface of the object. The optical detectors are positioned and oriented to receive scattered light scattered along paths lying in detection planes which are perpendicular to each other and perpendicular to the surface of the object. Signal processing electronics are provided to convert the light received by the detectors into analog signals which are multiplexed, converted to digital signals, filtered and then compared to preselected thresholds to determine the existence of any defects in the surface.

39 Claims, 6 Drawing Sheets

MODULAR SURFACE INSPECTION METHOD AND APPARATUS USING OPTICAL FIBERS

TECHNICAL FIELD

The present invention relates generally to a method and apparatus for surface inspection, and particularly relates to a method and apparatus for optical surface inspection of rolled sheet metal products.

BACKGROUND OF THE INVENTION

Modern manufacturing methods allow for very high production rates of rolled sheet metal products, such as aluminum, brass, and steel. Indeed, modern metal rolling equipment and techniques are capable of rolling sheet metal at thousands of feet per minute. Not surprisingly, monitoring the quality of sheet metal so produced represents a formidable challenge. These very high production rates make unworkable the traditional method of monitoring the manufactured goods, namely having a human inspector look carefully at the surface of the sheet metal (also known as a web) as it rolls off the mill.

The concept of replacing a human inspector for detecting flaws in moving webs with an optical detection system is known. Such optical detection systems typically have a source of light trained on the surface of the web and a detector element for detecting reflected or scattered light. For detecting flaws in rather wide material webs, such as rolled sheet metal, it has been known in the art to use a scanning beam of laser light to traverse the width of the material web.

U.S. Pat. No. 4,511,803 of Röss et al. discloses a fault detection apparatus for material webs in which laser light is scanned back and forth at very high speeds to create a line of light and the light reflected from the surface of the web is filtered with a hologram to allow the apparatus to detect scattered light for the detection of surface faults. Unfortunately, scanning techniques are generally unsatisfactory for inspecting very rapidly moving webs because the scanning equipment, although capable of rapidly scanning back and forth, generally is unable to scan quickly enough to inspect the entire surface of the web without missing some areas. Simply put, the scanning techniques are complex and are not able to keep up with the very rapidly moving rolled sheet metal.

In addition to the above identified problem of ensuring that the entire sheet is inspected, a surface inspection system also faces the task of reliably distinguishing defects from good surfaces and distinguishing both the type and magnitude of the defect. Furthermore, the environment of a typical metal rolling plant is harsh, particularly in the area of the rolling mill itself, with the rolled sheet metal often being hot and giving off oily fumes.

Accordingly, it can be seen that a need remains for a method and apparatus for surface inspection, particularly inspection of rolled sheet metal products, which is able to inspect the entire surface of the sheet metal despite very high production rates, and which is able to reliably distinguish the existence, type, and magnitude of a defect, while doing so in the harsh environment of a metal rolling plant. It is to the provision of such a method and apparatus that the present invention is primarily directed.

SUMMARY OF THE INVENTION

Briefly described, in a preferred form the present invention comprises an apparatus for inspecting the surface of an object which is moving in a direction of travel relative to the apparatus. The apparatus includes a light source for generating a line of light extending substantially across the width of the surface of the object and generally transverse to the direction of travel, with the light impinging on the surface of the object at an angle of incidence which lies in an illumination plane generally upstanding from the surface of the object. A first optical detector means is provided for detecting light scattered from the line of light by the surface of the object along a first path which lies in a first detection plane generally upstanding from the surface of the object. A second optical detector means is provided for detecting light scattered from the line of light by the surface of the object along a second path lying in a second detection plane generally upstanding from the surface of the object.

Preferably, the apparatus comprises a modular sensing head assembly including one or more sensing head modules, with each of the sensing head modules including one or more sensing stations. Each sensing station has mounted therein a diode laser or an LED (light emitting diode) acting as a light source and creating a short line of light. The LED's are arranged so that the individual short lines of light from the LED's cooperate to form a long line of light extending across as much of the web as desired, preferably across the entire web. The apparatus also preferably includes a third optical means for detecting scattered light. Each of the first, second, and third optical detector means comprises one or more optical sensors located at each sensing station and trained on the short line of light generated by each light source shining on the surface of the object.

The optical sensors are associated with detector amplifiers and variable gain stages to create a usable signal representing the amount of light scattered from the line of light along the particular path. Electronic circuitry is provided for evaluating this signal in light of pre-established minimum and maximum threshold levels. By using at least two optical detector means, and preferably three optical detector means, a characteristic "signature" of each type and magnitude of defect can be established and these signatures can be compiled in a table. The observed signals can be compared with the previously developed table of known defect signatures to determine the type and severity of the present defect.

Preferably, the first optical detector means is positioned in a region where less light is reflected from the surface of the web than adjacent regions so that the "signal" representing light reflected or scattered from a defect is more easily distinguished from the "noise" representing the light reflected or scattered by the surface in the absence of defect. This positioning takes advantage of the fact that most metals exhibit a polycrystalline structure, with individual crystals or "grains" adjoining one another at grain boundaries in a grain pattern. During rolling, the grains near the surface are stretched to a significant extent in the direction of rolling, causing the grains to become rather elongate and resulting in an approximately periodic structure. That periodic structure causes the reflected light signal resulting from a narrow, collinated light beam impinging on the surface to resemble a diffracted light beam from a coarse diffraction grating. The resulting scattered signal creates a sheet of light whose plane is perpendicular to the direction of elongation and the sheet metal surface. The width of the sheet of light (in the direction of grain elongation) is defined by the width and shape of the incident light beam. By placing a detector element in a region slightly displaced from the light plane, scattered light can be detected more effectively.

By constructing the apparatus to be modular, the apparatus can be easily adapted to span material webs of various widths, while employing repetitive components. Also, by using a continuous line of light rather than scanning with a single beam of light, the entire surface of the web can be inspected reliably, without missing areas.

Preferably, the apparatus includes a housing for containing the various optical elements, with the interior of the housing being blackened to absorb reflected light. Also, the interior of the housing is pressurized with air to prevent harmful vapors from entering the housing and damaging the various electronic and optical components.

In another form, the invention comprises a method for inspecting the surface of an object and comprises the steps of generating a line source of light and shining the line source of light onto the surface of the object to project a line of light on the surface of the object. Light scattered from the line of light by the surface of the object is detected in first and second detection planes generally upstanding from the surface of the object. Light detected in the first and second detection planes is converted to first and second electrical signals and the signals are filtered to remove noise. The electrical signals are then processed to detect the existence of a defect on the surface of the object. Preferably, the electrical signals are compared with pre-established "signatures" of various defect types to determine the type of defect detected.

Accordingly, it is an object of the present invention to provide a surface inspection method and apparatus which is able to inspect the entire surface of the object to be inspected in spite of a rather high rate of relative movement between the object to be inspected and the apparatus.

It is another object of the present invention to provide a method and apparatus for surface inspection which is effective for reliably distinguishing defects from good surfaces and for distinguishing both the type and magnitude of the defect.

It is another object of the present invention to provide a method and apparatus for inspecting surfaces which is reliable in the face of a harsh operating environment.

It is another object of the present invention to provide a method and apparatus for surface inspection which can be adapted easily to a wide variety of web widths.

It is a further object to provide signal processing electronics which allow spatial filtering to be done on-line as applied to surface inspection.

Other objects, features, and advantages of the Present invention will become apparent upon reading the following specification in conjunction with the accompanying drawing figures.

BRIEF DESCRIPTION OF THE DRAWING FIGURES

DETAILED DESCRIPTION

Figure 1:
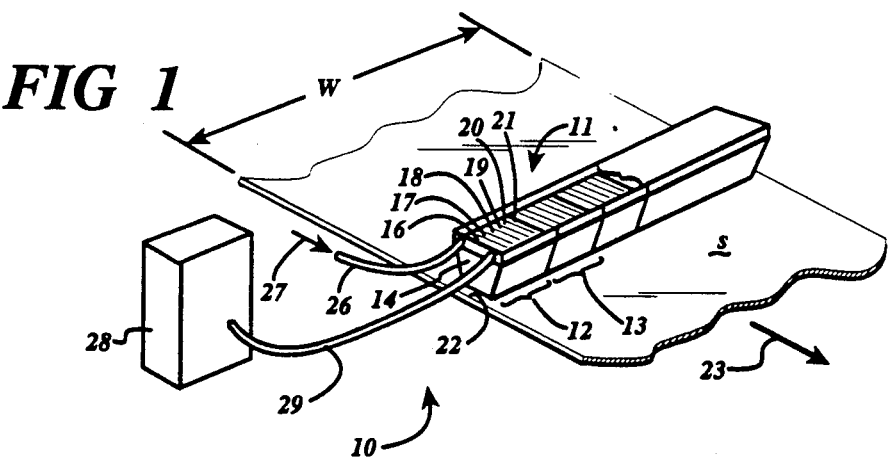
FIG. 1 is a perspective, schematic illustration of a surface inspection apparatus according to a preferred form of the present invention, showing a portion of the apparatus positioned over a moving web of material to be inspected.

Referring now in detail to the drawing figures, in which like reference numerals represent like parts throughout the several views, FIG. 1 shows a surface inspection apparatus 10 according to a preferred form of the invention. The surface inspection apparatus 10 includes a modular sensing head assembly indicated at 11 made up of individual sensing head modules, such as modules 12 and 13. The modules are attached end to end to one another to construct an assembly of suitable length for spanning the width W of a web of rolled sheet metal product S. Each of the modules is generally box-shaped with top, bottom, and two-side walls. With the exception of the modules at each end of the assembly, the modules do not have end walls so that the modules can be joined together to define a continuous open interior chamber. The outermost or end modules of the modular sensing head assembly 11 are fitted with end plates, such as end plate 14 attached to module 12. In this way, the modules together define an enclosure or housing.

Each of the modules includes a number of sensing stations, such as sensing stations 16–21 of module 12. Each of the sensing stations comprises a means for generating a short line of light and sensor means for detecting scattered light therefrom, as will be discussed in more detail below. The sensing stations are arranged so that the short line of light emanating from each of the sensing stations adjoin each other to form a continuous line of light 22 extending across substantially the entire width of the sheet metal S. The line of light 22 is perpendicular to the direction of travel 23 of the sheet metal S beneath the modular sensing head assembly 11.

An air passageway 26 communicates with an interior region of the modular sensing head assembly 11 for providing air under pressure to the interior of the modular sensing head assembly. By adding air under pressure, as schematically depicted by arrow 27, the interior of the modular sensing head assembly can be charged with positive pressure to prevent harmful vapors from finding their way into the interior of the modular sensing head assembly, thereby protecting the components within the assembly from damage from harmful gases. This is particularly important in applications involving rolled sheet metal because the sheet metal often is quite hot and carries a thin film of oil. The oil is partially evaporated by the heat, giving rise to oily vapors which can soil and contaminate electronic and optical components.

A console 28 contains electronic circuitry for controlling operation of the modular sensing head assembly and for processing information received therefrom, which electronic circuitry will be discussed in more detail below in connection with FIGS. 5-9. Console 28 is connected with the modular sensing head assembly 11 by means of cabling mounted within a protective conduit 29.

Figure 2A:
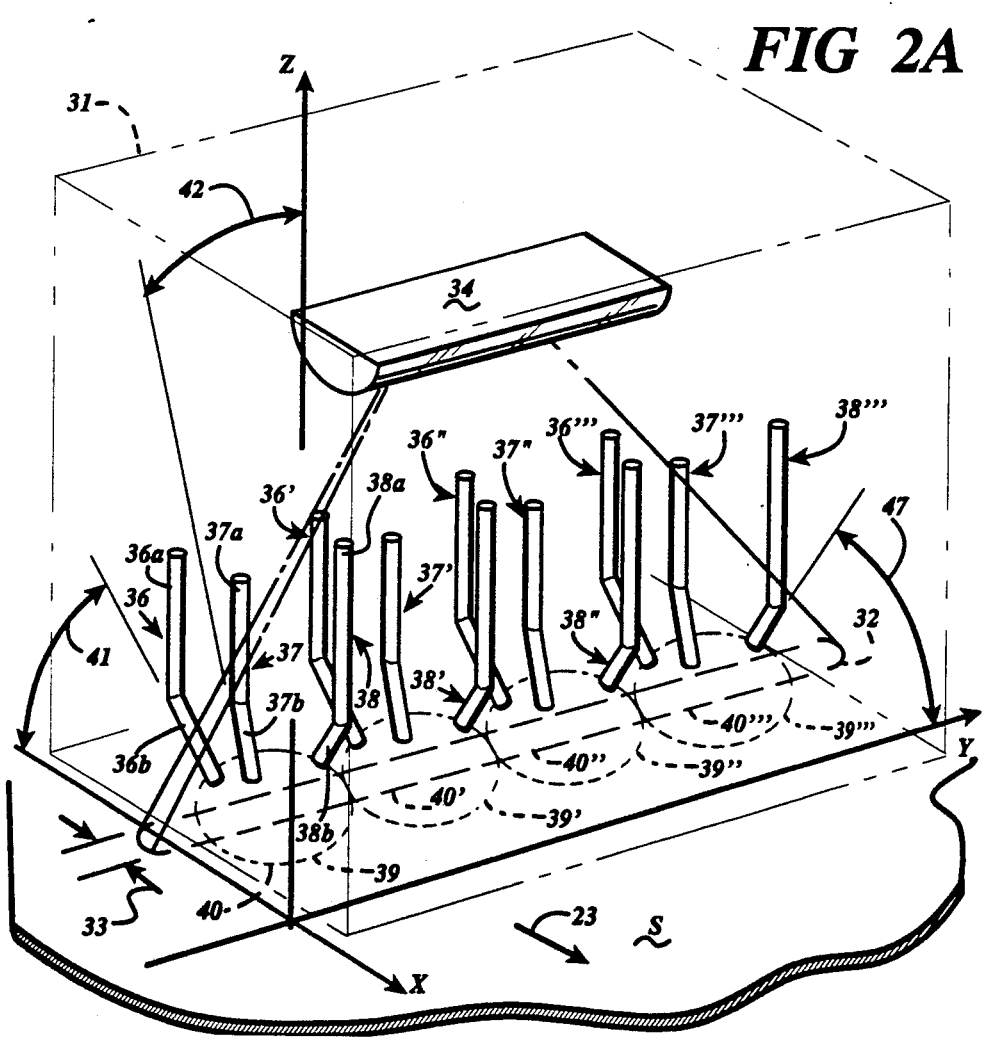
FIG. 2A is a schematic, perspective illustration of a sensing station portion of the apparatus of FIG. 1.
Figure 2B:
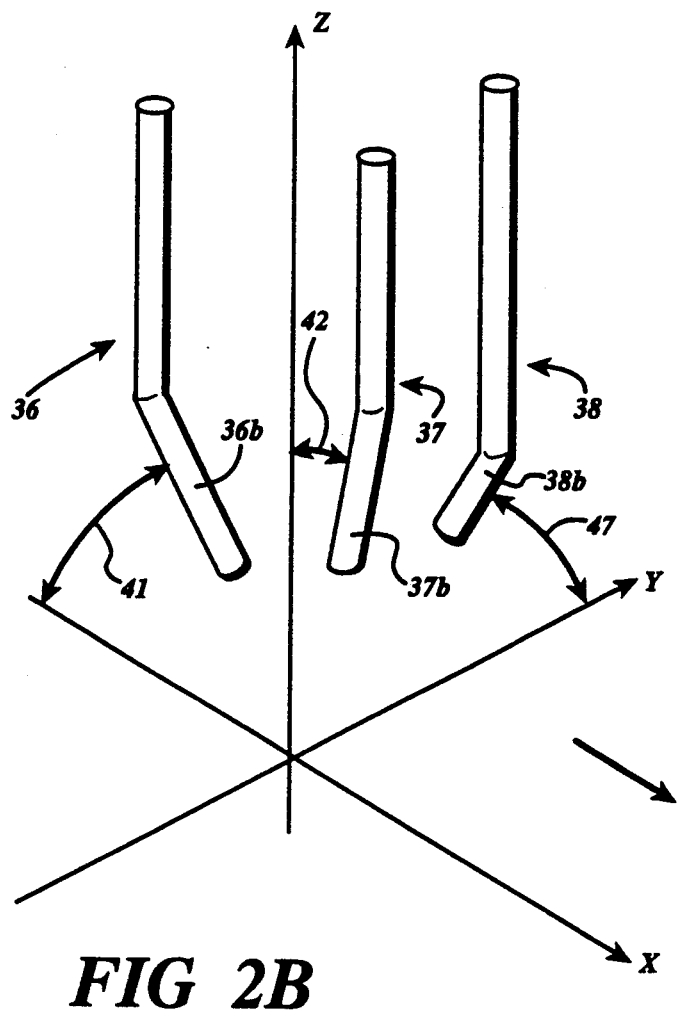
FIG. 2B is a perspective, schematic illustration of a portion of the sensing station of FIG. 2A.
Figure 2C:
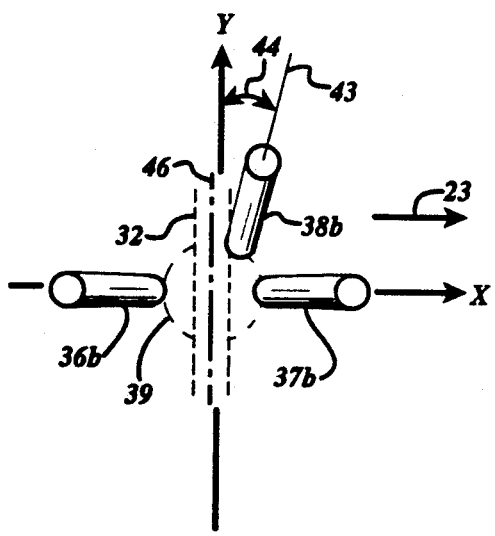
FIG. 2C is a plan view of the sensing station portion shown in FIG. 2B.

Referring now specifically to FIGS. 2A, 2B, and 2C, the details of a typical sensing station are considered. As shown in FIG. 2A, a portion 31 of a sensing station is depicted in dashed lines and is superimposed on X, Y and Z coordinate axes. FIG. 2A shows, at least in the Y direction, a complete sensing station. However, in the X and Z directions only a portion of the sensing station is illustrated in FIG. 2A for clarity. FIG. 2A shows a short line of light 32 impinging on the surface of the sheet metal, the line of light having a thickness 33 of approximately 0.8 mm. and a length (in the Y direction) of approximately 25 mm. As will be discussed in more detail in connection with FIG. 4, the line of light 32 is created with the use of a pair of cylindrical lenses, such as cylindrical lens 34.

The line image of light 32 impinges on the upper surface of the sheet metal S perpendicularly thereto and normal to the direction of travel 23. The line of light 32 extends slightly beyond the side edges of the sensing station in the Y direction so that the lines of light of adjacent sensing stations overlap one another slightly to create an uninterrupted line of light extending across the width of the sheet metal S. In considering this overlapping feature, it is important to realize that the sensing stations are not defined in the Y direction by physical walls, but rather that the sensing stations are considered to be collections of elements, as will be described more fully below.

Each sensing station has one line of light 32 extending thereacross in the Y direction. Associated with each line of light 32 are a number of triplets of optical detectors comprising fiber optic elements positioned and oriented to detect light scattered from the line of light by the surface of the sheet metal. For example, a first triplet comprises first, second, and third fiber optic elements 36, 37, and 38. Similarly, a second triplet comprises fiber optic elements 36', 37 and 38', a third triplet comprises fiber optic elements 36", 37", and 38", and a fourth triplet comprises fiber optic elements 36''', 37''', and 38'''. The fiber optic elements are conventional large core elements. By using fiber optic elements, the sensing stations can be made quite compact and the variously oriented detectors can be positioned quite close to the surface of the sheet metal.

Each of the fiber optic elements includes an upper portion which may be flexed and routed in any desired configuration and a lower portion which is oriented in a specific orientation and aimed towards a portion of the line of light 32. For example, fiber optic element 36 includes an upper portion 36a and a lower portion 36b. Likewise, elements 37 and 38 include upper and lower portions 37a, 38a and 37b, 38b. The remaining fiber optic elements 36'-38', 36"-38", and 36'''-38''' also include similar upper and lower portions. In laboratory experiments conducted to establish the feasibility of the invention, large core fiber optical cables having diameters ranging from 0.1 mm to 1.0 mm were found to work well.

The orientation of the lower portions of these fiber optic elements is made clear by consideration of lower elements 36b, 37b, and 38b. As best shown in FIG. 2C, lower portion 36b lies in a detection plane coincident with the XZ plane and therefore is perpendicular to the surface of the sheet metal S and parallel to the direction of travel 23. Furthermore, lower portion 36b is oriented at an angle 41 with respect to the surface of the sheet metal S or the X axis (see FIGS. 2A and 2B). The angle 41 preferably is 45° and can be as small as 15° or as great as 60°.

Lower portion 37b of fiber optic element 37 also lies in the detection plane coincident with the XZ plane (see FIG. 2C). As shown in FIG. 2A, lower portion 37b is positioned to the same side of the line of light 32 as is lower portion 36b of fiber optic element 36. The lower portion 37b of fiber optic element 37 is oriented at a small, near-normal angle 42 of between 5° and 15°, preferably 10°, with respect to the Z axis.

Alternatively, lower portion 37b can be positioned on an opposite side of the line of light 32, as is shown in FIG. 2B. However, lower portion 37b should not be positioned in a plane perpendicular to the direction of rolling, as will be made clear in the discussion of FIG. 3.

Figure 3:
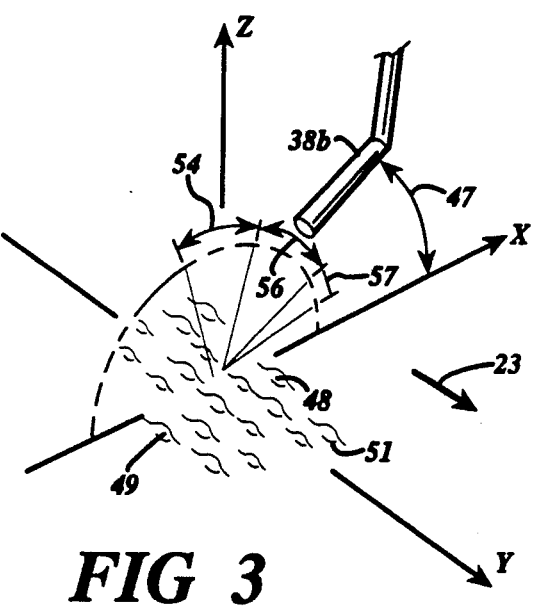
FIG. 3 is a schematic, perspective illustration of fiber optic element portion of the apparatus of FIG. 2A, showing the position of the fiber optic element in relation to a typical interference pattern from a beam of light being "diffracted" by an elongate grain structure of a surface of a rolled sheet metal product.

Lower portion 38b of fiber optic element 38 lies in a plane which is generally transverse to the X axis, though not perpendicular thereto and not parallel to the YZ plane. This is so because should the lower portion 38b lie in a plane which is parallel to the YZ axis, in order for the lower portion 38b to be pointed at the line of light 32, the lower portion 38b of the fiber optic element would have to be coplanar with the line of light emanating from the cylindrical lens 34. This would cause a shadow or gap in the line of light and is undesired. Thus, as is shown in FIG. 2C, lower portion 38b lies in a detection plane 43 which is generally transverse to the direction of travel 23 and which detection plane is perpendicular to the surface of the sheet metal. Plane 43 also is oriented with respect to the YZ plane at a slight angle 44, preferably approximately 5°. The lower portion 38b also is offset slightly from the axis of elongation 46 of the line of light 32 so as to avoid causing the undesired shadow. As shown in FIGS. 2A and 2B and 3, lower portion 38b is positioned in region 56 and is oriented at an angle 47 with respect to the XY plane of between 15° and 60°, preferably 45° in order to detect certain kinds of defects more easily.

FIG. 3 illustrates the importance of the position of lower portion 38b of fiber optic element 38a. In FIG. 3, a number of crystalline grains, such as grains 48 and 49, of a rolled sheet metal product are shown. The grains adjoin one another at grain boundaries, such as grain boundary 51. As was discussed in the above Summary of the Invention, the grains near the surface are stretched during rolling in the direction of rolling to a significant extent, causing the grains to become rather elongate. As shown in FIG. 3, the grains are elongated in the direction of the Y axis (the direction of travel 23). Typically, the grains have an aspect ratio of approximately 5; that is, the grains are five times as long as they are wide. When viewed in the direction of Y, the grain pattern results in a generally undulating surface, with the peaks and valleys of the undulating surface extending lengthwise in the Y direction.

A light source (unshown in FIG. 3) directing a beam of light perpendicularly onto the undulating surface causes the light to be preferentially scattered into a pattern similar to that produced by an ordinary coarse diffraction grating. The pattern is characterized by a relatively bright sheet of light of maximum intensity at the path of specular reflection (in region 54) and generally decreasing in intensity progressing from regions 54 to 57 and to the surface. The pattern is characterized by an intensity profile that is limited lengthwise in the direction of elongation of the grain pattern by the shape of the incident light beam. By placing the lower portion 38b of the detector element slightly displaced away from the light sheet (i.e. in the direction of grain elongation) scattered light can be more easily detected because the diffracted light is concentrated in other areas. Thus, there is no need to filter out diffracted light from scattered light collected at this location.

The positions and orientations of the various fiber optic elements as shown were established in reference to detecting defects in rolled sheet aluminum. For other materials, including aluminum alloys, steel, brass, etc., slightly different positions and orientations might be more appropriate.

By training two or more, in this case three, detectors on one spot, the existence, magnitude, and type of defect is more reliably detected. This is so because a particular defect might be difficult to detect from one orientation, though it might be readily detected from other orientations. Also, redundancy helps to make the detection more reliable. As an alternative to arranging the multiple detectors to actually be trained on the same spot, it is possible to effectively obtain the same result by training the detectors on a linear series of spots chosen downstream of one another, so that by time shifting the signals produced by the detectors in a manner to correspond to the speed of the sheet meal, the apparatus effectively looks at one spot with multiple detectors.

Figure 4:
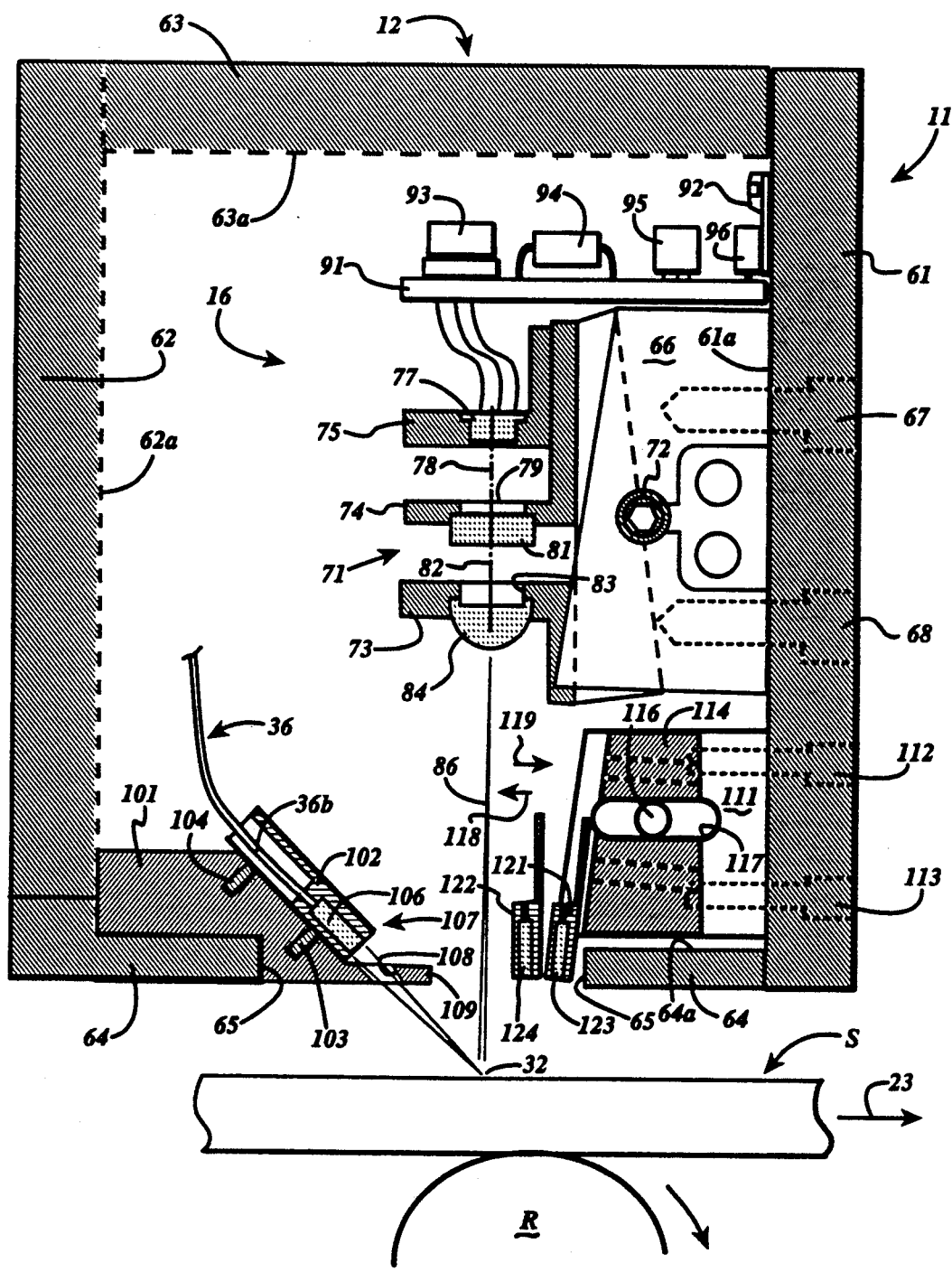
FIG. 4 is a side sectional view of the apparatus of FIG. 1.

FIG. 4 shows a cross-section of the modular sensing head assembly 11 taken through a sensing station 16. The sensing head module 12 includes side walls 61 and 62 and an upper wall or roof panel 63. A floor panel 64 defines an opening therein 65 to allow light to be transmitted from within the sensing head module 12 to the surface of the sheet metal product and to receive light reflected straight back into the sensing head module. Such light reflected straight back into module 12 is not desired and would create a large DC reading if collected by the optical detectors. The interior surfaces of the side walls 61 and 62, the roof panel 63, and the floor panel 64, such as interior surfaces 61a, 62a, 63a, and 64a, are all blackened to absorb reflected light energy. Also, beam dumps can be utilized, if desired.

The modular sensing head assembly 11 is positioned over the sheet metal product S in the vicinity of a roller R to minimize variations in the orientation of the upper surface of the sheet metal product S and the spacing ("standoff") of the assembly 11 from the surface due to bending or sagging of the sheet metal product. Thus, the upper surface of the sheet metal product S remains relatively flat, parallel, and at constant spacing to the floor panel 64 in the vicinity of the modular sensing head assembly 11.

A first mounting bracket 66 is secured to vertical side wall 61 by bolts 67 and 68. A bracket element 71 is adjustably mounted to the bracket 66 by bolt 72. Bracket element 71 includes first, second, and third ledges 73, 74, and 75, with the ledges positioned above one another. A light source 77 is positioned in ledge 75 in a manner to direct a beam of light along path 78. Preferably, the light source 77 comprises a laser diode producing light energy having a wavelength of 780 nanometers. The beam of light 78 passes through an opening 79 formed in the intermediate ledge 74 and is focused by a cylindrical lens 81. The focused light emanating from cylindrical lens 81 proceeds along path 82 through an opening 83 formed in lower ledge 73 and is further focused by cylindrical lens 84. Cylindrical lenses 81 and 83 are oriented perpendicularly to each other; i.e., their axes of elongation lie perpendicular to each other. This orientation of the two cylindrical lenses allows the lenses to act in concert to focus the light emanating from the light source into a narrow, elongated line image of light traveling along path 86 in one direction or plane. The line image of light makes smaller the light source seen by the detectors in relation to the size of the defect which the apparatus is looking for and thereby improves the signal-to-noise ratio.

Infrared GaAlAs LED's also are good candidates for the light sources as they have extremely high output at wavelengths of approximately 880 nanometers, which is near the peak responsivity of silicone photodetectors, have long lifetimes compared with incandescent sources, are suited for efficient coupling to optical fibers, have an invisible and spectrally narrow output that permits the use of narrow bank optical filters to reduce or eliminate ambient light interference, and they are relatively inexpensive. They also provide a well-defined cone of light which is easy to control via lenses 81, 84. However, the laser diodes are preferred because the light output is more powerful and is easier to focus.

A circuit board 91 is mounted to side wall 61 by a fastener 92 and contains electronic components 93, 94, 95 and 96 for controlling the output of the diode laser 77 described in more detail below with regard to the diode laser source driver circuit of FIG. 6.

A support base 101 is securely mounted to floor panel 64 to one side of the path 86 of light streaming from the lower cylindrical lens 84. A detector mounting bracket 102 is secured to the support base 101 by threaded fasteners 103 and 104. A graded refractive index lens ("GRIN lens") or waveguide 106 is mounted at a lower end 107 of detector mounting bracket 102. Lower portion 36b of a fiber optic element 36 is mounted in detector mounting bracket 102 so that the free end of the lower portion 36b faces and abuts one end of the GRIN lens 106. The function of the GRIN lens 106 is to collect and focus light into the fiber optic element lower portion 36b. As was discussed earlier, lower portion 36b lies in a detection plane perpendicular to the surface of the sheet metal and parallel to the direction of travel. Preferably, element 36b is oriented 45° from the surface of the sheet metal product. An opening 108 is formed in a footer portion 109 of the support base 101 for allowing light scattered from the surface of the sheet metal product S to be received in the GRIN lens 106.

A mounting bracket 111 is mounted to side wall 61 by bolts 112 and 113. A second bracket element or platform 114 is movably secured to mounting bracket 111 by a bolt 116. Bolt 116 extends through a slot 117, thereby allowing second bracket element 114 to move back and forth in the directions of direction arrows 118 and 119.

A first detector mounting bracket 121 is securely mounted to the second bracket element 114 in a manner similar to that of detector mounting bracket 102. A second detector mounting bracket 122 also is mounted to the second bracket 114 in a similar manner. Detector mounting brackets 121 and 122 are adapted to retain fiber optic elements, which have been omitted in FIG. 4 for clarity of illustration. The first and second detector mounting brackets 121 and 122 carry GRIN lenses 123 and 124 at their ends in a manner similar to that of mounting bracket 102.

The first and second mounting brackets 121 and 122 are oriented and positioned to locate the fiber optic elements 37 and 38 in the orientations depicted in FIGS. 2B and 2C. Thus, the fiber optic elements are trained on (aimed at) the line of light 32 impinging on the surface of the sheet metal product. In FIG. 4, the second bracket element 112 is shown retracted somewhat in the direction of direction arrow 119 for purposes of illustration. However, in use, the second bracket element 114 would be extended in the direction of direction arrow 118 so as to train the GRIN lenses 123 and 124 and the unshown (at least in FIG. 4) fiber optic elements 37 and 38 on the line of light 32.

Crosstalk, the pickup of optical signals from the adjacent LED's, is prevented by the use of collection waveguides with an appropriate numerical aperture. The numerical aperture of an optical waveguide is the angular range of the optical rays entering the end of the waveguide that can be confined and guided. At angles exceeding that of the numerical aperture, the entering light rays are not guided. Conversely, the numerical aperture or acceptance angle also is defined as the angular extent of the cone of light emitted from an optical waveguide. By properly specifying the numerical aperture of the collection fibers (or in this case the combination of the fiber optic cables and the GRIN lenses), only the scattered signal emanating from a specific illuminated spot is captured by the collection waveguide and crosstalk from an adjacent element is minimized.

The numerical apertures of the light collection elements (the fiber optic cables and the GRIN lenses) are represented as cones originating at the light collection elements and spreading outwardly therefrom. Where the surface of the object intersects the cones of the three light collection elements 36–38 at various angles, three ellipses are defined thereby. Thus, each light collection element can "see" light coming up from within an ellipse on the surface of the object. Collectively, these three ellipses are shown schematically in FIGS. 2A and 2C as circles 39, 39', 39", and 39''' shown in dashed lines. The circles roughly represent the surface area observed and they overlap one another slightly in the Y direction. As shown in FIG. 2A, the intersection of the circles with the line of light 32 results in individual pixels 40, 40', 40", and 40'''. Each pixel is monitored by three optical "channels", corresponding to, for example, fiber optic elements 36, 37 and 38. The pixels overlap one another slightly in the Y direction.

A second source of optical noise originates with the specular and the "diffracted" components. Direct interception of these is avoided by the careful placement of the collection waveguides. However, the specular or "diffracted" component hitting a surface within the optical head may be scattered back towards the rolled metal surface and that light in turn scattered towards the collection waveguides. Therefore, the reflected (specular) component of the illumination beam should be trapped and absorbed by using beam dumps and optically black surfaces, as described above. The shaped illumination beam facilitates the use of beam dumps to be designed into the sensing head.

Standoff distances, the separation of the sensing elements from the sheet surface, of 0.25 inches to a few inches were used in laboratory tests. In terms of collection efficiency, standoff distances of 0.25 to 0.50 inches proved to be most satisfactory. Over that range, variations of ±2 millimeters in the standoff distance, such as might be encountered with surface motion of the web, were tolerated with no appreciable signal level changes.

The collection efficiency of the optical waveguides is a function of both the standoff distance and the numerical aperture of the waveguides. The numerical aperture defines the collection angle of the optical waveguide. Rays entering the waveguide at angles exceeding those corresponding to the numerical aperture will not be guided. Thus, as the collection fiber is moved closer to the surface, the numerical aperture limits the collection efficiency. In contrast, the collection efficiency at large standoff distances is limited by the waveguide's physical aperture. Thus, an optimum standoff range exists, and in terms of practical waveguides and waveguide apertures, the 0.25 inch to 0.50 inch range is near optimum.

The small angle scattering measurements are sensitive to tilting of the sheet metal surface. Typically, the small angle scattering is measured at 5 to 10 degrees away from the specular or the "diffracted" component. A tilt in excess of two degrees can create erroneous signals. Thus, the preferred surface inspection should be performed over or near a roller to avoid the "waves" that appear in the unsupported regions between the rollers. To minimize this effect, fiber optic elements 37b and 38b can be oriented to look at the surface from a backscatter position.

The shaped illumination beam allows the scattered signals to be spatially separated from the specular and diffracted components. A small angle scattering intensity increases as the angle between the detector position and the direction of propagation defined by the specular or diffracted component decreases. By using a converging illumination beam that is focused to a minimum spot size after reflection from the surface of the object, the collection angle can be minimized. This technique makes the detection of scattered light easier, while isolating and concentrating the reflected and diffracted components. To detect very weakly scattering defects, the collection efficiency of the small angle scattered light detector can be further enhanced by using an aperture stop to block the specular or diffracted component from being detected by the light detector and a small lens can be employed to collect the small angle scattered signal which bypasses the stop. This technique effectively increases the optical collection efficiency and the signal-to-noise ratio.

Various modifications can be made to the optical parts of the apparatus. For example, a glass window can be provided for covering the lower opening 65. Also, two or four sensors can be employed, rather than a triplet, for detecting scattered light at each spot. Furthermore, the individual LED's positioned within the sensing stations can be replaced with one or multiple light sources remotely located and communicating light to the cylindrical lens through fiber optic cables, and such is shown schematically in FIG. 6. This has the safety advantage of allowing all electronic components to be mounted remotely from the sensing head assembly, which can be a great advantage when inspecting surfaces in the presence of volatile solvents or lubricants. On the other hand, a single elongated light source in the form of a long bulb or a filament line bulb positioned above a long slit can be employed.

Figure 5:
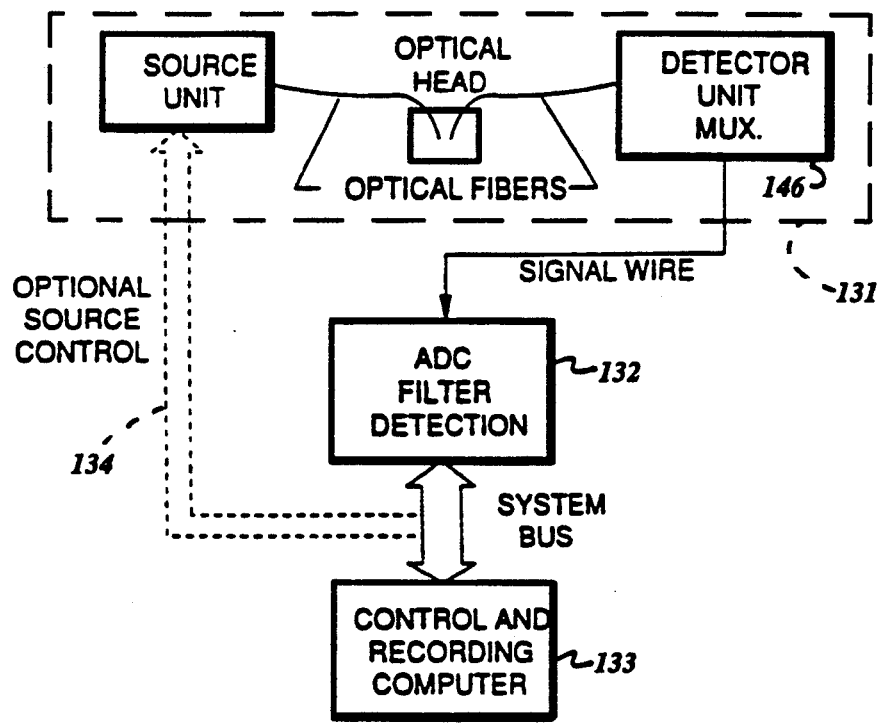
FIG. 5 is a schematic block diagram of the surface inspection apparatus of FIG. 1.

Having described the optical and mechanical aspects of the invention, attention is now turned to the electronic and signal processing aspects. Referring specifically to FIG. 5, the electronics of the apparatus includes three major sub-systems, namely detector analog electronics indicated at 131, a digital signal processing subsystem 132, and a computer 133 for logging data. Source control means indicated at 134 are provided for controlling individual light sources for each sensing station. This allows individual level control stabilization which facilitates accurate comparison between adjacent elements.

Figure 6:
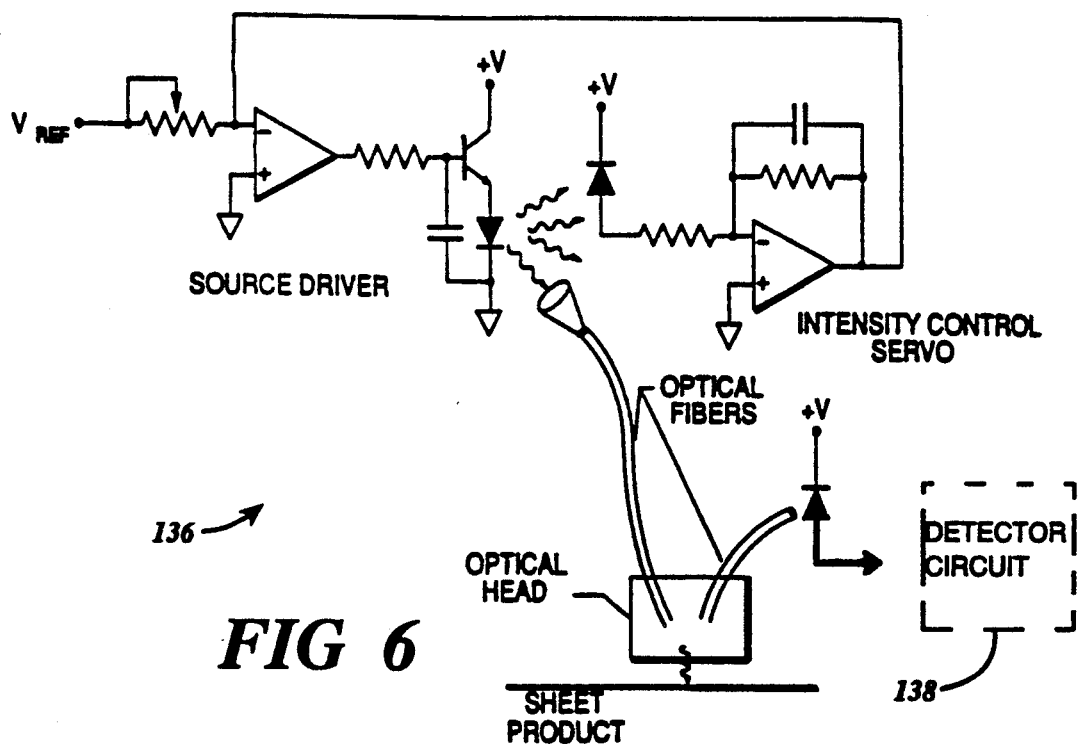
FIG. 6 is a schematic electrical diagram of a control circuit used to control the output of the light source of the apparatus of FIG. 1.

Referring now to FIG. 6, a source driver circuit 136 is shown for controlling the output of laser diode 77. The circuit ensures that the variation in the response of each sensing element is less than the variation in response due to the minimum defect that is to be recognized by the apparatus. This is accomplished by balancing the output of each laser diode. One practical way of accomplishing this is to use individual illuminating laser diodes each having its own intensity control. This type of intensity control can be used to compensate for different output characteristics of the light sources, as well as different response curves of the detectors, and differences in the transfer functions of the optical systems (e.g., the cylindrical lens) associated with each sensing station. A proper nominal level can be established by inspecting a control surface. The intensity control is accomplished by intercepting a portion of the light emitted from the laser diode and returning it to a feedback photodiode/phototransistor circuit as shown in FIG. 6. The gain of the feedback circuit is adjusted automatically using the variable resistor to urge the output of the laser diode toward a preselected value.

Figure 7:
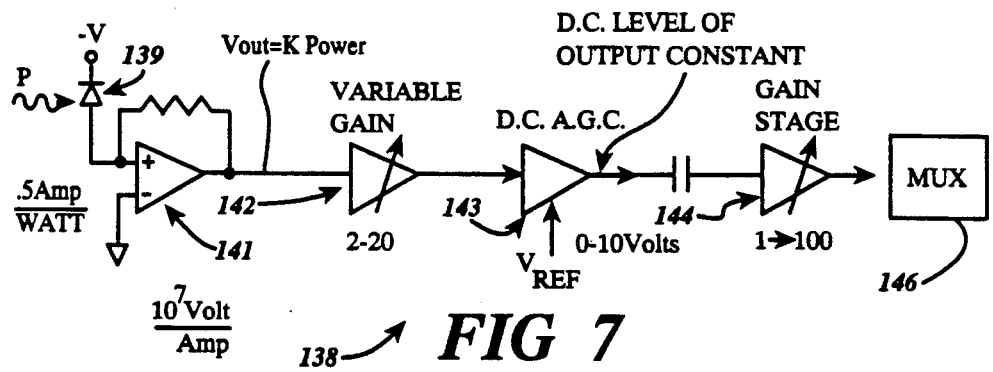
FIG. 7 is a schematic electrical diagram of a detector circuit used to detect light scattered from the surface being inspected and to amplify a signal produced by the optical detectors of the apparatus of FIG. 1.

FIG. 7 shows detector circuit 138 for converting the scattered light collected through one of the fiber optic elements into a useful signal, each fiber optic element having its own associated detector circuit. The circuit includes a 0.5 amp-per-watt photodiode 139 for converting the detected light into an electrical signal. The electrical signal from the photodiode 139 is boosted preferably about $10^7$ volts/amp by pre-amp 141, and the signal is then in turn acted upon by a variable gain stage 142 and then a direct current automated gain control 143. The variable gain stage 142 and the direct current automated gain control amplifier 143 serve to maintain the D.C. level of the output of gain control 143 equal to the constant reference voltage, $V_{ref}$. This compensates for small variations due to dirt and the like in the received light signal to maintain the electrical signal at a relatively constant level. The direct current average gain control amplifier 143 is A/C coupled to a second variable gain stage 144 to remove background and to all other deviations. The output from gain stage 144 is directed to multiplexor 146 shown in FIG. 8.

Figure 8:
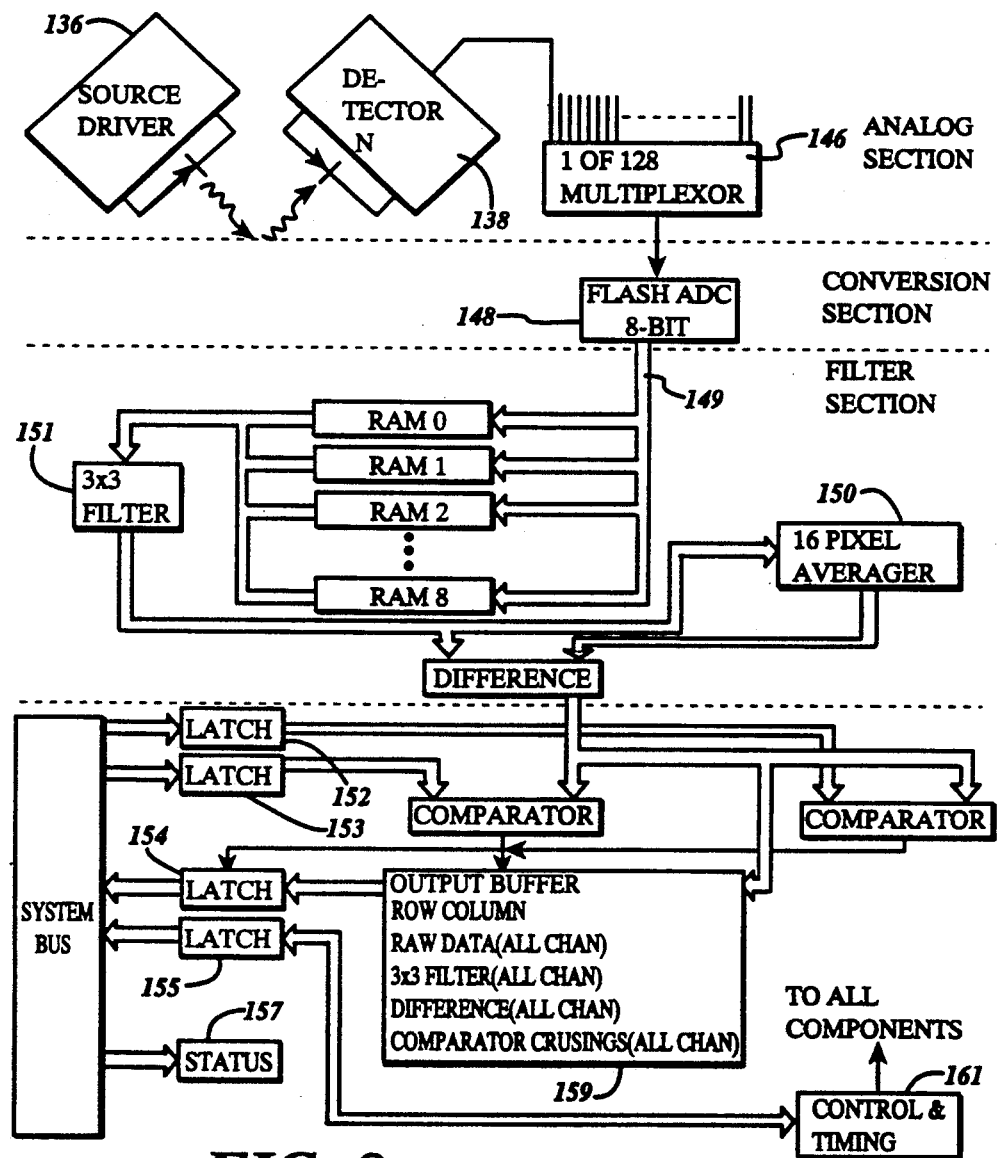
FIG. 8 is a schematic diagram of a signal processing portion of the apparatus of FIG. 1.

As shown in FIG. 8, the analog signals from each of the detector circuits 138 of one channel are multiplexed with multiplexor 146 with the signals from similar detector units from adjacent sensing elements of a module, such as module 13, onto a single electrical line. This electrical line thus carries a raster image of the surface as seen by a particular type of detector, i.e., the close angle detectors lying in the XZ plane or the 45° detectors lying just off the YZ plane. The multiplexed signals from one type of detector for the module are one channel of the signal processing electronics. The multiplexed signals from the two other types of detectors comprise two other channels of information. Each channel of information is processed through its own circuit, such as that shown in FIG. 8, including its own multiplexor.

The multiplexor 146 is adapted to multiplex the signals from one channel of fiber optic elements onto a single line. Since each fiber optic element of a channel monitors a single pixel of a discrete length, each multiplexor 146 can multiplex a channel of signals covering a length determined by the product of the number of signals multiplexed and the length of the individual signals (pixels). In a prototype apparatus, 32 pixels of 0.1 inch long produce a multiplexed signal covering 3.2 inches. Also, a small but finite length of time is required for the multiplexor to complete one cycle and this "duty cycle" time is dictated by the rapidity of a timing signal used to control operation of the multiplexor. As shown in FIG. 8, a control and timing module 161 is provided for controlling and timing the operation of various components of FIG. 8, including those of multiplexor 146. These control and timing functions are carried out by an unshown clock driven by an unshown crystal oscillator. The clock should be selected to provide a rapid enough duty cycle of the multiplexor 146 to inspect sheets to ensure that no portion of the web is missed, even if the web is moving at maximum speed. Thus, the width of the pixel (in the X direction) divided by the duty cycle time (which is related to clock speed) should exceed the web speed to ensure that no areas are missed.

The analog signal carried by the electrical line from the multiplexor 146 is then converted into an n bit parallel data stream using an analog-to-digital converter ("ADC") 148. Preferably, an 8-bit flash converter is used because of the adequate resolution, speed, and availability of such a flash converter. The parallel data stream 149 exiting the flash ADC is then filtered with digital filters. Preferably, spatial filters are used to perform a bandpass operation. This filter is a combination of a 3×3, approximately Gaussian two-dimensional spatial filter and a linear spatial filter of 8 or 16 pixels in width, and this is depicted as 3×3 filter 151 and the 16-pixel averager 150, respectively in FIG. 8. These filters produce, in real time, spatial bandpass functions of the parallel data stream. The data streams emanating from these filters are compared to quasi-fixed values ("thresholds"). The thresholds are held in latches, such as latches 152 and 153. The thresholds held in these latches can be changed dynamically by the control computer. If a threshold is exceeded, then the value of each data stream (i.e., all three channels) is passed on to the output buffer 159 to be saved along with the appropriate occurrence data, such as web position, time, etc. If none of the threshold values are exceeded, the data values associated with that particular sensing element are discarded. In this manner, only unusual pixel data are saved, thereby dramatically reducing the amount of data passed on to the next stage (i.e., the computer). The threshold values used in the comparisons can be predetermined or dynamically changed to fit varying data conditions. The comparators are designed to trap data representing signals which either rise above an expected range or fall below an expected range, with the expected range representing the typical signal measured on a normal, defect-free surface.

The data associated with signals falling outside the expected range are stored and then passed to the processor controlling that particular bank of detectors for suitable classification processing to sort the occurrence into one of several defect types. In many cases, the classification will be defined by a lookup table. To develop the lookup table, one would inspect known defects with the system to develop characteristic "signatures" for the various types of defects. Such look-up tables of characteristic signatures vary as a result of different compositions of the sheet metal product, standoff distance, pixel width, pixel length, etc. The measured signals of actual production sheet metal defects can then be compared with the developed lookup table to determine the type of defect present. Following classification, the defect types, location, size, etc., can be stored for further reference.

A control register 155 is coupled to the system bus for controlling what action is to be taken with respect to the data. For example, the control register determines whether to accept data, to accept no data, to start or stop sensing operations, to select which lines of the multiplexor are to be activated, and to flag defect data to be stored. A status register 157 also is available to allow the control computer to monitor the state of the various system control signals.

The logging computer has the capability of permanently storing the data, of maintaining a running tally of the types of defects detected, or maintaining only a present history log for this particular sheet. The computer also can set the comparator values used by the comparators.

The output buffer 159 is large so that it can store substantial amounts of data. The buffer should be large enough to store raw data from all three channels, 3×3 filter data from all channels, the state of all threshold latches, row and column data by pixel and difference data.

Figure 9A:
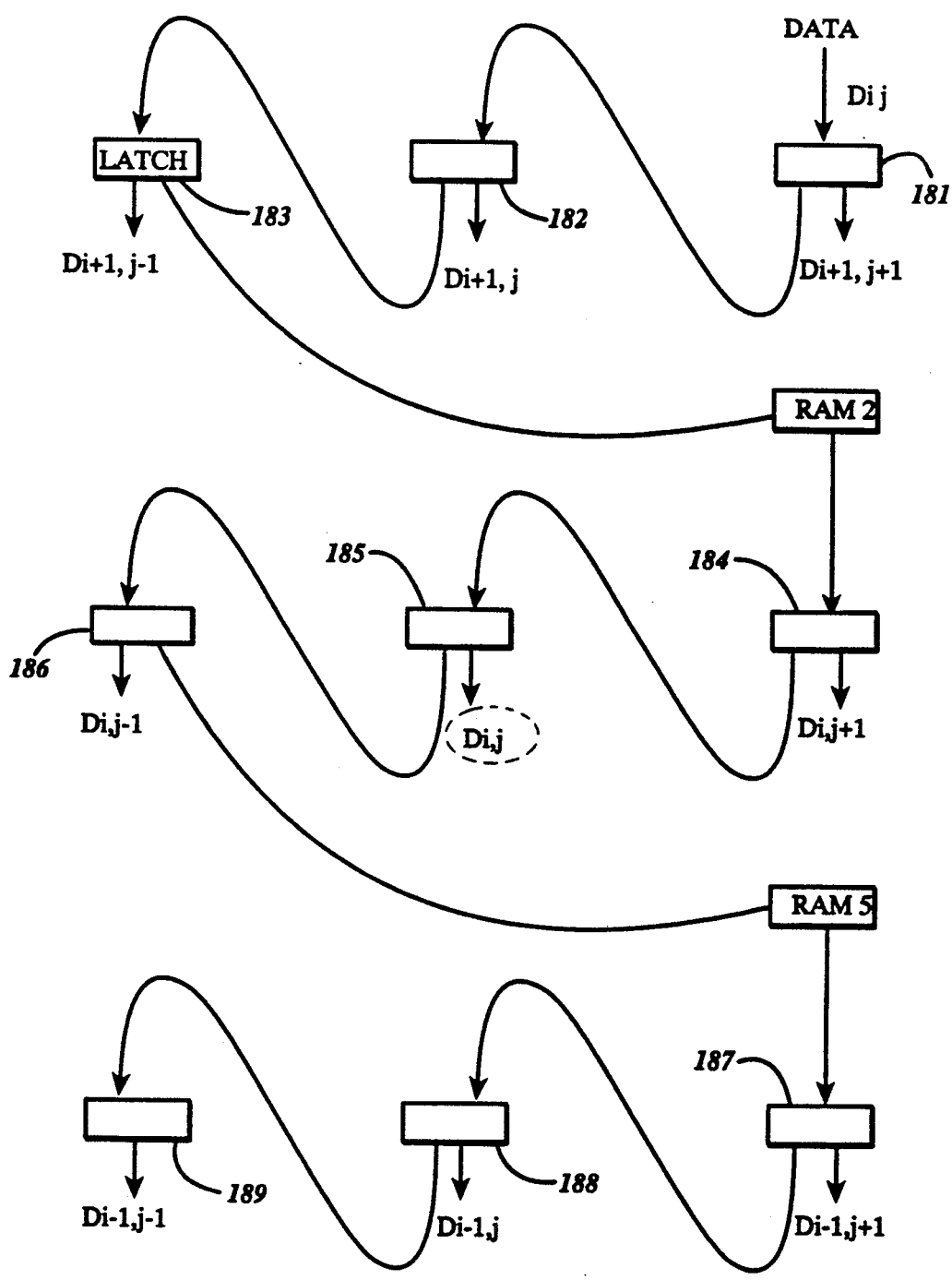
FIGS. 9A and 9B are schematic diagrams of a filtering scheme employed in the signal processing of FIG. 8.

FIG. 9A shows the preferred embodiment of the filter section of FIG. 8 including the 3×3 filter, the pixel averager and the process for obtaining difference data.

Data from the flash ADC 148 of the conversion section of FIG. 8 is sent to a first series of pixel latches 181, 182, 183 in sequence. Data is clocked through these latches in sequence in a manner similar to a shift register. Each latch has a corresponding output from which the value stored in the latch may be read. As data is clocked out of the last latch 183 of the first series of latches, it is sent to and stored in random access memory, designated RAM 2. Data from RAM 2 is clocked through a second series of three latches 184, 185, 186 in sequence in a manner similar to the first series of three latches. The output of latch 186 is sent to a second random access memory, designated RAM 5, where the data is stored until needed to be sent to the third series of three latches 187, 188, 189. Each of the latches of the second and third series of latches also has a corresponding output from which the value stored in the latch may be read.

Figure 9B:
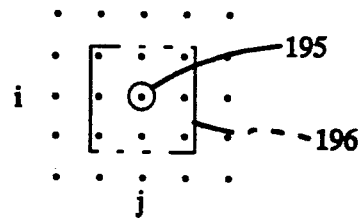

In FIG. 9B an array of points or pixels is shown. Each pixel represents the section of the line image of light at its location of impingement on the surface of the object being viewed by a given triplet of optical detectors. At any given moment the apparatus of the present invention is determining whether a defect exists on the surface of the object at a given point or pixel i,j 195. The apparatus determines the presence or absence of a defect at pixel i,j by also considering readings taken at the pixels adjacent pixel i,j in the array 196. The values obtained from the readings of the nine pixels of the array 196 can be obtained from the nine latches of FIG. 9A with the value from the reading of pixel i,j coming from latch 185. The 3×3 filter then calculates a value $H_{ij}$ from all nine readings D using the following formula:

$$H_{ij} = 1/16\,(D_{i+1,j+1} + D_{i+1,j-1} + D_{i-1,j+1} + D_{i-1,j-1}) +$$
$$2/16\,(D_{i+1,j} + D_{i-1,j} + D_{i,j+1} + D_{i,j-1}) + 4/16\,(D_{i,j})$$

The calculation of the value $H_{i,j}$ by the 3×3 filter serves to smooth the signal out. The random access memory RAM 2, and RAM 5 serve to synchronize the readings D from the 3×3 filter so that, for example, the reading pixel i−1, j in the row behind, but in the same column as, pixel i,j is obtained from latch 188 at the same time the reading from pixel i,j is obtained from latch 185 and the reading from pixel i+1, j in the row above, but in the same column as, pixel i,j is obtained from latch 182.

Pixel averager 150 filters out low-frequency background noise for pixel i,j by the following formula:

$$B_{ij} = H_{ij}/16 + 15/16(B_{i-1,j})$$

A difference is then taken between the value $H_{ij}$ from the 3×3 filter 151 and the value $B_{ij}$ from the pixel averager 150 as follow:

$$\text{Difference} = H_{ij} - B_{ij}$$

By taking this difference, the apparatus gets away from drift in the system and slow changing functions in the system such as changes in lighting. As can be seen, the filtering section apparatus of the signal processing electronics allows spatial filtering to be done on-line. It is the difference value that is compared to preselected thresholds stored in latches 152 and 153 to determine the presence or absence of a defect. After signal processing, the computer can be programmed to take information stored for pixel i,j and by looking at information stored for the adjacent pixels to determine the size and type of defect. Enough memory should be provided in buffer 159 to store data for several pixels.

Applicants have conducted laboratory studies of test samples to establish the feasibility of the invention in a production environment. The laboratory studies were conducted with a limited number and type of surface defects, and at least in reference to the defects studied, the studies have shown that defects exhibiting only very slight modifications to the surface structure are generally only detectable through a small angle of scattering, such as with detector elements 37, when the illumination plane is perpendicular to the surface structure.

Defects with more severe surface damage, but still retaining the basic surface structure, are characterized by an increase in the amplitude of the scattered signal. Defects characterized by a general obliteration of the surface structure tend to result in scattering in all directions, while other defect types associated with more severe surface deformation and flawing of the material surface exhibit scattering perpendicular to the original surface structure. The latter tends to be easily detected by observing scattering at large angles and parallel to the usual surface features. By observing scattering at different angles, in either planes parallel or perpendicular to the direction of rolling, discrimination of the various defects into general classes or types is possible.

Defects in production samples from metal rolling plants range from difficult to extremely difficult to see visually. The present apparatus is capable of locating most of the typical defects found in production of sheet metal. The experimental results have shown that the angular scattering characteristics and the signal amplitudes are related to the type of defect and to the severity of its associated surface damage. Based on those characteristics, some discrimination can be accomplished in real-time using the thresholding of the various signals after spatial filtering, as described above. Each type of defect has a characteristic signature based on the relative strengths of the optical scattering at the different angles. The thresholding is adjusted to separate the defects into as many classes as possible and then to separate them from the defect-free regions of the sheet. When the threshold signature indicates a defect, all of the associated sensor values are saved for later analysis to further classify the defect as to type, size, and severity. In addition to the angular scattering profile, the spatial morphology of the defect area provides classification and severity information. For example, the defect areas and samples exhibiting "roll skid marks" tended to be a few millimeters in length and the width of signals displayed on an oscilloscope reflect those dimensions. Comparisons of "skid roll mark" defects with "pit" defects having dimensions of less than a millimeter show that the apparatus has the ability to discriminate based on the length of the defect (in the direction of web motion) and on the size of the defect (transverse to the direction of web motion).

The above-described discrimination and classification techniques are amenable to real-time signal processing through the use of parallelism in the signal analysis. Additional discrimination and classification can be accomplished by the data logging computer as a second priority task (the first priority task being the logging of the defect data) in pseudo real-time. That is, if the defect frequency rates are not too high, the data logging computer can perform the additional classification algorithms between logging of the defects. In some instances, this final classification will have to be completed after the conclusion of the rolling operation has been completed while the coil of rolled sheet metal is being removed. This additional classification time, if necessary, is not expected to exceed a few minutes at a maximum. Examples of this type o classification include the examining of adjacent sensing elements to determine the dimensional characteristics of the defect types, computing ratios of the scattering intensities from the various sensors and calculating the occurrence period of the defects for determining the method and location of the defects creation.

While the invention has been disclosed in preferred form, it will be obvious to those skilled in the art that many modifications, additions, and deletions may be made therein without departing from the spirit and scope of the invention as set forth in the appended claims.

We claim:

1. An apparatus for inspecting the surface of an object moving in a direction of travel relative to said apparatus, said apparatus comprising:

light source means for generating a line of light on the surface of the object generally transverse to the direction of travel, with the line of light impinging the surface of the object at an angle of incidence lying in an illumination plane generally upstanding from the surface of the object;

first optical detector means for detecting light scattered from the line of light by the surface of the object along a first path lying in a first detection plane generally upstanding from the surface of the object; and second optical detector means for detecting light scattered from the line of light by the surface of the object along a second path lying in a second detection plane generally upstanding from the surface of the object, said apparatus comprising a modular sensing head assembly including at least two sensing head modules, with each of said sensing modules comprising a plurality of sensing stations.

2. An apparatus as claimed in claim 1 further comprising third optical detector means for detecting light scattered from the line of light by the surface of the object along a third path lying in said second detection plane.

3. An apparatus as claimed in claim 1 wherein said first path lying in said first detection plane is oriented between 15° and 60° with respect to the surface of the object.

4. An apparatus as claimed in claim 1 wherein said second path lying in said second detection plane is oriented between 15° and 60° with respect to the surface of the object.

5. An apparatus as claimed in claim 1 wherein said first path lying in said first detection plane is oriented between 75° and 85° with respect to the surface of the object.

6. An apparatus as claimed in claim 2 wherein first and third optical detector means are positioned on opposite sides of said illumination plane and trained on a common spot.

7. An apparatus as claimed in claim 1 wherein said illumination plane is generally perpendicular to the surface of the object and normal to the direction of travel.

8. An apparatus as claimed in claim 1 wherein said first detection plane is generally transverse to the direction of travel and said second detection plane is generally aligned with the direction of travel.

9. An apparatus as claimed in claim 1 wherein said first detection plane is perpendicular to the surface of the object and oriented to be within 15° of normal relative to the direction of travel.

10. An apparatus as claimed in claim 1 wherein said second detection plane is perpendicular to the surface of the object and is generally parallel to the direction of travel.

11. An apparatus as claimed in claim 1 wherein the object to be inspected is rolled sheet metal and wherein said first optical detector means is positioned to one side of a sheet of light "diffracted" in a pattern set up by the line of light impinging on the surface of the sheet metal.

12. An apparatus as claimed in claim 1 wherein said light source means comprises at least one diode laser.

13. An apparatus as claimed in claim 1 wherein said light source means comprises at least two light emitting diodes arranged adjacent one another for creating an extended line of light.

14. An apparatus as claimed in claim 1 wherein said line of light extends substantially completely across the surface of the object.

15. An apparatus as claimed in claim 1 further comprising light generating means and lens means for focusing light emitted from said light generating means into a line of light.

16. An apparatus as claimed in claim 15 wherein said means for focusing comprises first and second cylindrical lens means oriented perpendicularly to each other and disposed between said light generating means and the surface of the object.

17. An apparatus as claimed in claim 1 wherein said first and second optical detector means each comprise optical wave guide means for collecting light scattered along said first and second paths.

18. An apparatus as claimed in claim 17 further comprising lens means mounted adjacent an end of each of said optical wave guide means nearest the object for collecting scattered light.

19. An apparatus as claimed in claim 17 further comprising a detector amplifier and a variable gain stage.

20. An apparatus as claimed in claim 1 wherein said light source means comprises a light emitting diode mounted at each of said sensing stations.

21. An apparatus as claimed in claim 20 wherein said first and second optical detector means each comprise at least two optical sensors positioned at each of said sensing stations.

22. An apparatus as claimed in claim 1 further comprising a housing containing at least some of said light source means, said first optical detector means, and said second optical detector means, said housing having an opening adjacent the object.

23. An apparatus as claimed in claim 22 further comprising means for introducing air under pressure to an interior region of said housing.

24. An apparatus as claimed in claim 22 wherein said housing includes interior surfaces and wherein said interior surfaces are blackened to minimize reflection of light.

25. An apparatus for inspecting the surface of an object moving in a direction of travel relative to said apparatus, said apparatus comprising:
light source means for generating a line of light on the surface of the object generally transverse to the direction of travel, with the line of light impinging the surface of the object at an angle of incidence lying in an illumination plane generally upstanding from the surface of the object;
first optical detector means for detecting light scattered from the line of light by the surface of the object along a first path lying in a first detection plane generally upstanding from the surface of the object; and
second optical detector means for detecting light scattered from the line of light by the surface of the object along a second path lying in a second detection plane generally upstanding from the surface of the object,
wherein said first and second optical detector means each comprise a plurality of sensors for creating electronic signals and fiber optic means for communicating scattered light to said sensors, said apparatus further comprising multiplexor means associated with said sensors for multiplexing said signals.

26. An apparatus as claimed in claim 13 further comprising electronic means for controlling the output of said light emitting diodes to balance the intensity of light from said light emitting diodes.

27. An apparatus as claimed in claim 26 wherein said electronic means for controlling the output of said light emitting diodes is adapted to monitor the output and to control the output with a feedback control loop.

28. An apparatus as claimed in claim 25 further comprising means for comparing said signals with pre-established thresholds to detect the existence of a defect and means for comparing signals of a detected defect with pre-established characteristic signals of known defect types to classify the detected defect by type.

29. An apparatus for inspecting the surface of an object comprising:
means for generating a source of light;
means for shining the source of light onto the surface of the object to project a line of light on the surface of the object;
first means for detecting light scattered from the line of light by the surface of the object in a first detection plane generally upstanding from the surface of the object;
second means for detecting light scattered from the line of light by the surface of the object in a second detection plane generally upstanding from the surface of the object;
means for converting the scattered light detected by said first and second means for detecting light for creating first and second electrical signals, respectively;
means for filtering the first and second electrical signals to remove noise therefrom;
means for multiplexing the first and second electrical signals; and
means for processing the first and second electrical signals to detect the existence of a defect on the surface of the object.

30. An apparatus as claimed in claim 29 further comprising means for comparing the first and second signals with pre-established defect characteristics to classify the type of defect detected.

31. An apparatus as claimed in claim 29 wherein the means for processing the signals comprises means for comparing the signals with pre-established thresholds.

32. An apparatus as claimed in claim 29 wherein the second means for detecting scattered light in the second detection plane comprises means for detecting scattered light along a first path in the second detection plane, the first path being oriented at an angle of between 15° and 60° with respect to a plane perpendicular to the surface of the object, said apparatus further comprising a third means for detecting scattered light in the second detection plane along a second path oriented at an angle of between 5° and 15° with respect to a plane perpendicular to the surface of the object.

33. An apparatus as claimed in claim 23 wherein the object to be inspected is a rolled sheet metal product having an elongated grain structure and wherein said first means for detecting scattered light in a first detection plane comprises an optical detector positioned outside of a sheet of light of a pattern set up by "diffraction" of light by the elongated grain structure of the rolled sheet metal product.

34. An apparatus as claimed in claim 29 further comprising a third means positioned in one of said first and second detection planes for detecting light scattered from the line of light by the surface of the object.

35. A method for inspecting the surface of an object comprising the steps of:
 (a) generating a source of light;
 (b) shining the source of light onto the surface of the object to project a line of light on the surface of the object;
 (c) detecting light scattered from the line of light by the surface of the object in a first detection plane generally upstanding from the surface of the object;
 (d) detecting light scattered from the line of light by the surface of the object in a second detection plane generally upstanding from the surface of the object;
 (e) converting the scattered light detected in the first and second detection planes to first and second electrical signals, respectively;
 (f) filtering the first and second electrical signals to remove noise;
 (g) multiplexing the first and second electrical signals; and
 (h) processing the first and second electrical signals to detect the existence of a defect on the surface of the object.

36. A method as claimed in claim 35 further comprising the step of comparing the first and second signals with pre-established defect characteristics to classify the type of defect detected.

37. A method as claimed in claim 35 wherein the step of processing the signals comprises comparing the signals with pre-established thresholds.

38. A method as claimed in claim 35 wherein the step of detecting scattered light in the second detection plane comprises detecting scattered light along a first path in the second detection plane, the first path being oriented at an angle of between 15° and 60° with respect to a plane perpendicular to the surface of the object, the method further comprising the steps of detecting scattered light in the second detection plane along a second path oriented at an angle of between 5° and 15° with respect to a plane perpendicular to the surface of the object and converting the scattered light detected in the second detection plane along a second path into a third electrical signal.

39. A method as claimed in claim 33 wherein the object to be inspected is rolled sheet metal having an elongated grain structure and wherein the step of detecting scattered light in a first detection plane comprises the step of positioning an optical detector outside of a sheet of light of a pattern set up by "diffraction" of light by the elongated grain structure of the rolled sheet metal.

* * * * *